(12) United States Patent
Riddell et al.

(10) Patent No.: US 10,602,995 B2
(45) Date of Patent: Mar. 31, 2020

(54) MEDICAL IMAGING METHOD VARYING COLLIMATION OF EMITTED RADIATION BEAM

(71) Applicant: GENERAL ELECTRIC COMPANY, Schenectady, NY (US)

(72) Inventors: Cyril Riddell, Issy-les-Moulineaux (FR); Yves Lucien Trousset, Palaiseau (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 817 days.

(21) Appl. No.: 14/958,678

(22) Filed: Dec. 3, 2015

(65) Prior Publication Data

US 2016/0228074 A1 Aug. 11, 2016

Related U.S. Application Data

(63) Continuation of application No. PCT/US2014/039908, filed on May 29, 2014.

(30) Foreign Application Priority Data

Jun. 5, 2013 (EP) .................................... 13305755

(51) Int. Cl.
*A61B 6/06* (2006.01)
*G21K 1/04* (2006.01)
(Continued)

(52) U.S. Cl.
CPC .................. *A61B 6/06* (2013.01); *G21K 1/02* (2013.01); *G21K 1/04* (2013.01); *H01J 35/025* (2013.01); *H01J 37/023* (2013.01)

(58) Field of Classification Search
CPC .. A61B 6/00; A61B 6/06; A61B 6/405; A61B 6/52; A61B 6/5258; A61B 6/5282;
(Continued)

(56) References Cited

U.S. PATENT DOCUMENTS 4,086,494 A 4/1978 Malak
4,203,037 A 5/1980 Gur et al.
(Continued)

FOREIGN PATENT DOCUMENTS

| NO | 2004092768 A2 | 10/2004 |
| WO | 2007120744 A2 | 10/2007 |
| WO | 2009141766 A2 | 11/2009 |

OTHER PUBLICATIONS

International Search Report and Written Opinion for corresponding WO Appln. No. PCT/US2014/039908, dated Sep. 24, 2014, 11 pages.
(Continued)

*Primary Examiner* — Anastasia Midkiff
(74) *Attorney, Agent, or Firm* — Fletcher Yoder, P.C.

(57) ABSTRACT

This invention relates to a medical imaging method comprising: emitting a radiation beam from a radiation source of a rotating gantry, preferably of a rotating C-arm, on a volume of interest, varying collimation of said emitted radiation beam so as to change at least part-time a field of view of said emitted radiation beam so that there are at least a first part and a second part of said volume of interest such that, when said first part of said volume of interest is imaged, said second part of said volume of interest is shuttered, and when said second part of said volume of interest is imaged, said first part of said volume of interest is shuttered.

14 Claims, 3 Drawing Sheets

(51) Int. Cl.
*G21K 1/02* (2006.01)
*H01J 35/02* (2006.01)
*H01J 37/02* (2006.01)

(58) Field of Classification Search
CPC ............ G21K 1/00; G21K 1/02; G21K 1/025;
G21K 1/04; G21K 1/046; H01J 35/00;
H01J 35/02; H01J 35/025; H01J 37/00;
H01J 37/02; H01J 37/023; H01J 37/04;
H01J 37/045; H01J 37/0455
See application file for complete search history.

(56) References Cited

U.S. PATENT DOCUMENTS

| | | |
|---|---|---|
| 6,320,929 B1 | 11/2001 | Von Der Haar |
| 6,339,636 B1 | 1/2002 | Ogawa |
| 2004/0057554 A1 | 3/2004 | Bjorkholm |
| 2004/0120457 A1* | 6/2004 | Karellas ............... A61B 6/06 378/62 |
| 2004/0264626 A1* | 12/2004 | Besson ............... A61B 6/032 378/4 |
| 2005/0053188 A1* | 3/2005 | Gohno ............... A61B 6/032 378/15 |
| 2005/0169432 A1 | 8/2005 | Groh et al. |
| 2007/0195935 A1 | 8/2007 | Vermeulen et al. |
| 2007/0280408 A1* | 12/2007 | Zhang ............... A61B 6/025 378/10 |
| 2008/0025458 A1* | 1/2008 | Virshup ............... A61B 6/032 378/6 |
| 2008/0075225 A1 | 3/2008 | Kalender |
| 2008/0118023 A1* | 5/2008 | Besson ............... A61B 6/032 378/8 |
| 2008/0298539 A1 | 12/2008 | Nakanishi |
| 2008/0317212 A1 | 12/2008 | Kuehn et al. |
| 2009/0190714 A1* | 7/2009 | Partain ............... A61B 6/032 378/19 |
| 2009/0256078 A1 | 10/2009 | Mazin |
| 2010/0119033 A1* | 5/2010 | Li ............... A61B 6/06 378/5 |
| 2011/0019798 A1 | 1/2011 | Kang et al. |
| 2012/0257709 A1 | 10/2012 | Oota et al. |
| 2012/0269318 A1 | 10/2012 | Flohr et al. |
| 2015/0346120 A1* | 12/2015 | Vogler ............... G01N 23/203 250/358.1 |

OTHER PUBLICATIONS

European Search Report for corresponding EP Appln. No. 13305755.4, dated Nov. 22, 2013, 9 pages.
Bushberg, "The essential physics of medical imaging, 3rd," Lippincott Williams & Wilkinds, XP-002716226, Nov. 20, 2011, 2 pages.

* cited by examiner

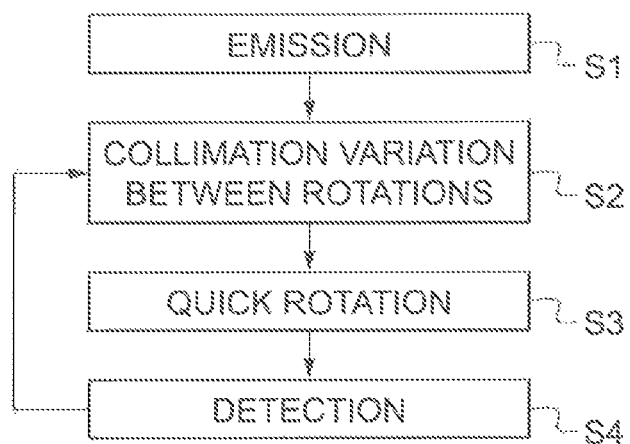
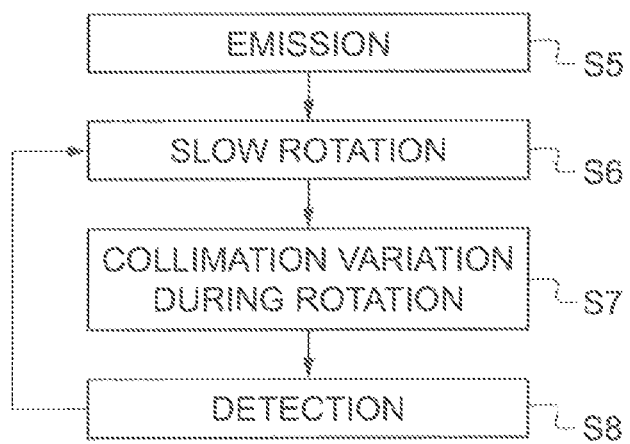

ly reduced, compared to the scattered radiation
obtained with a medical imaging method using no variation
of collimation of the emitted radiation beam or some variation of collimation of the emitted radiation beam but for
another purpose different from scattered radiation reduction.

MEDICAL IMAGING METHOD VARYING COLLIMATION OF EMITTED RADIATION BEAM

Single-use bioreactor systems are commonly used for cell culture applications. The growth and culture of mammalian cells, for instance, typically require a constant supply of adequate oxygen. Oxygen diffusion in culture media is a function of a liquid-to-air surface area when operating the bioreactor. Furthermore, oxygen transfer is limited by the liquid-to-air surface area and any shear forces created by agitation and/or sparging.

FIELD OF THE INVENTION

The invention relates to medical imaging methods and to associated medical imaging systems.

BACKGROUND OF THE INVENTION

According to a first prior art, for example described in U.S. Pat. No. 7,983,391B2, there is a movable radiation shield reducing radiation exposure. In a volume of interest, only a center part of higher interest is refreshed more often than a surrounding part of lower interest. The radiation detector is not rotating. There is radiation exposure lowering. However, there is no scattered radiation lowering for a given radiation exposure of the volume of interest.

According to a second prior art, for example described in U.S. Pat. No. 8,213,568B2, there is a dynamic collimator shuttering part of the emitted radiation beam to match the beginning and the end of the volume of interest in order to cancel radiation exposure of not needed parts which are just before the beginning of the volume of interest and just after the end of the volume of interest, when performing helical computed tomography. There is cancellation of radiation exposure of useless parts in the vicinity of the volume of interest. However, there is no scattered radiation lowering for a given radiation exposure of the volume of interest.

Several existing imaging methods use collimation variation of emitted radiation beam. But none of them use collimation variation of emitted radiation beam in order to reduce scattered radiation. None of them either use the specific type of collimation variation of emitted radiation beam used in the invention in order to reduce scattered radiation.

SUMMARY OF THE INVENTION

The object of the present invention is to alleviate at least partly the above mentioned drawbacks.

More particularly, the invention aims at proposing a specific collimation variation of the emitted radiation beam of the medical imaging system which allows for scattered radiation reduction.

In none of the methods proposed in the reviewed prior art can be found a varying or a dynamic collimation such that any first and second parts of a volume of interest to be imaged such that, when said first part of said volume of interest is imaged, said second part of said volume of interest is shuttered, and when said second part of said volume of interest is imaged, said first part of said volume of interest is shuttered.

It is thanks to those parts of a volume of interest to be imaged such that, when said first part of said volume of interest is imaged, said second part of said volume of interest is shuttered, and when said second part of said volume of interest is imaged, said first part of said volume of interest is shuttered, that the volume of interest can be easily imaged whereas the scattered radiation is reduced, and preferably substantially reduced, compared to the scattered radiation obtained with a medical imaging method using no variation of collimation of the emitted radiation beam or some variation of collimation of the emitted radiation beam but for another purpose different from scattered radiation reduction.

Using varying, or dynamic, collimation of the emitted radiation, for example X-ray, beam, is using a variable collimation during a tomographic acquisition. Indeed, a first set of tomographic acquisition with a given collimated emitted radiation beam is completed by an additional second set of measurements using a different collimation of this same emitted radiation beam. That way, dynamic collimation of the emitted radiation beam provides an extra degree of freedom when designing the sampling of tomographic data, all the more that it is fully compatible with patient or radiation source translation.

This object is achieved with a medical imaging method comprising: emitting a radiation beam from a radiation source of a rotating gantry, preferably of a rotating C-arm, on a volume of interest, varying collimation of said emitted radiation beam so as to change at least part-time a field of view of said emitted radiation beam so that there are at least a first part and a second part of said volume of interest such that, when said first part of said volume of interest is imaged, said second part of said volume of interest is shuttered, and when said second part of said volume of interest is imaged, said first part of said volume of interest is shuttered.

Preferably the volume of interest at the patient level corresponds to the sensitive surface of the radiation detector at the detection level, or at least to a part of this sensitive surface. The addition of said first and said second parts of volume of interest correspond to said sensitive surface of the radiation detector, or at least to part of this sensitive surface.

For said parts of said volume of interest, switching from imaged to shuttered or switching from shuttered to imaged, occurs by varying collimation.

Preferably most of parts of said volume of interest, advantageously all parts of said volume of interest can be shared out among couples of a said first part of said volume of interest and of a said second part of said volume of interest.

This object is achieved with a medical imaging system comprising: a rotatable gantry or C-arm comprising a radiation source and a collimating device, said radiation source being adapted to emit a radiation beam on a volume of interest when said gantry or C-arm rotates, said collimating device being adapted to vary collimation of said emitted radiation beam so as to change at least part-time a field of view of said emitted radiation beam so that there are at least a first part and a second part of said volume of interest such that, when said first part of said volume of interest is imaged, said second part of said volume of interest is shuttered, and when said second part of said volume of interest is imaged, said first part of said volume of interest is shuttered.

Preferred embodiments comprise one or more of the following features, which can be taken separately or together, either in partial combination or in full combination.

Preferably, said gantry or C-arm is associated to an examination table which stays immobile during gantry or C-arm rotation. The medical imaging method according to embodiments of the invention also works in situations where it is either difficult or uncomfortable to move the examination table. It also works well in situations where the examination table can only be moved very slowly.

Preferably, said gantry or C-arm is rotating so as to compute three dimensional imaging. Since, in this type of imaging, gantry or C-arm is rotating most of the time, there may be more constraints to vary collimation, but the scattered radiation reduction benefit is high enough.

Preferably, in a first alternative, said collimation is varied during each rotation turn of said gantry or C-arm. Here, preferably, the collimation variation is performed relatively often and quickly so that all collimation positions can be scanned at each rotating position of the rotating gantry or C-arm. That way, the whole volume of interest can be imaged, whereas the scattered radiation has been notably reduced compared to a more classical process without collimation variation. Compared to the next alternative, less rotations of gantry or C-arm are needed.

Preferably, in a second alternative, said collimation is varied between two rotation turns at a same axial position of said gantry or C-arm. Here, preferably, the collimation variation is performed relatively seldom, and can be performed slowly, so that only a single collimation position is kept during a full rotating turn of the rotating gantry or C-arm. That way too, the whole volume of interest can be imaged, whereas the scattered radiation has been notably reduced compared to a more classical process without collimation variation. Compared to the previous alternative, less frequent collimation variations are needed.

Preferably, said varying collimation is periodical, said gantry or C-arm rotation is periodical, and said varying collimation frequency is equal to or higher than the rotation frequency of said gantry or C-arm. This high relative varying collimation frequency allows for important scattered radiation reduction, since that way, most of the time a narrow collimation position is used to perform imaging.

Preferably, in an embodiment, said varying collimation changes said field of view size whereas said varying collimation does not change said field of view central position. Preferably, said varying collimation changes said field of view size such as to perform a modulation of the exposure intensity as in a bow-tie filtering on said emitted radiation beam.

Preferably, in another embodiment, said varying collimation changes said field of view central position whereas said varying collimation does not change said field of view size. That way, the type of imaging performed is the same than a more classical imaging with no collimation variation, but for a much lower scattered radiation.

Preferably, said varying collimation moves position of said emitted radiation beam so that it scans at least part of a sensitive surface of a radiation detector of said gantry or C-arm. Preferably, said scanning is a linear scanning, said scanning a single direction, said linear scanning preferably scanning a single line. This scanning of the sensitive surface of the radiation detector allows for taking advantage of part of or all the sensitive surface of a large radiation detector while lowering substantially the scattered radiation.

Preferably, said varying collimation moves respective positions of at least two of said emitted radiation beams so that they respectively scan complementary portions of at least part of a sensitive surface of a radiation detector of said gantry or C-arm. Using several emitted radiation beams is a way to increase and even multiply dynamic collimation frequency which otherwise could be limited by the collimation switching velocity and or by the image chain rotation speed. Indeed, the velocity would be increased by using several radiation, preferably X-ray, focal spots that would each expose a portion of the radiation detector. A simple implementation would use two focal spots, each exposing one half of the sensitive surface of the radiation detector.

Preferably, in an embodiment, said rotating gantry or C-arm makes full rotations. Preferably, in another embodiment, said rotating gantry or C-arm rotates alternatively clockwise and counter-clockwise.

Preferably, said varying collimation shutters a portion of said emitted radiation beam which is more than one third, preferably more than one half, more preferably more than two thirds, of said emitted radiation beam, and said varying collimation shutters said portion of said emitted radiation beam during at least part of imaging, preferably during all of imaging. That way, the relatively important portion of shuttered emitted radiation beam lowers all the more the scattered radiation.

Preferably, when a radiation detector of said gantry or C-arm receives said emitted radiation beam on a first part of its sensitive surface and is shuttered by said varying collimation on a second part of its sensitive surface, a level of radiation detected on said second part is computed as a level of scattered radiation which is then subtracted from a level of radiation detected on said first part. This has the same effect as a supplementary reduction of scattered radiation since part of scattered radiation is eliminated during subsequent signal processing.

Preferably, in an embodiment, said variably collimated emitted radiation beam transversal shape, transversal with respect to its propagation direction, forms a single window, preferably of constant size.

Preferably, in another embodiment, said variably collimated emitted radiation beam transversal shape, transversal with respect to its propagation direction, forms several different windows, preferably each of constant size, preferably immobile relatively to one another. This embodiment allows for better scattered radiation elimination during subsequent signal processing, because the level of unwanted scattered radiation can be estimated more precisely, since there is a succession of small and close adjacent zones of transparency to radiation and shuttering of radiation.

Preferably, said variably collimated emitted radiation beam transversal shape, transversal with respect to its propagation direction, forms one or more rectangular windows. This allows for simpler and more complete scanning of the sensitive surface of the radiation detector.

Preferably, said varying collimation is performed by several translating blades.

Further features and advantages of the invention will appear from the following description of embodiments of the invention, given as non-limiting examples, with reference to the accompanying drawings listed hereunder.

BRIEF DESCRIPTION OF THE DRAWINGS

FIG. 1 shows an example of an embodiment of a medical imaging method varying the collimation of the emitted radiation beam according to the invention.

FIG. 2 shows an example of another embodiment of a medical imaging method varying the collimation of the emitted radiation beam according to the invention.

DETAILED DESCRIPTION OF THE INVENTION

In all following part of the text, except if otherwise specified, when radiation is used, X-ray which is a specific radiation could be used instead as well. Both applications, on the one hand to radiation in general and on the other hand to X-ray in particular, are intended to be covered. In a similar way, when C-arm is mentioned, any other type of gantry, for example gantry of a computed tomography scanner, unless otherwise specified, could be used instead of the C-arm.

FIG. 1 shows an example of an embodiment of a medical imaging method varying the collimation of the emitted radiation beam according to the invention. The medical imaging method varying the collimation of the emitted radiation beam comprises a step S1 of emission, a step S2 of collimation variation between rotations, a step S3 of quick rotation, a step S4 of detection.

Figure 7:
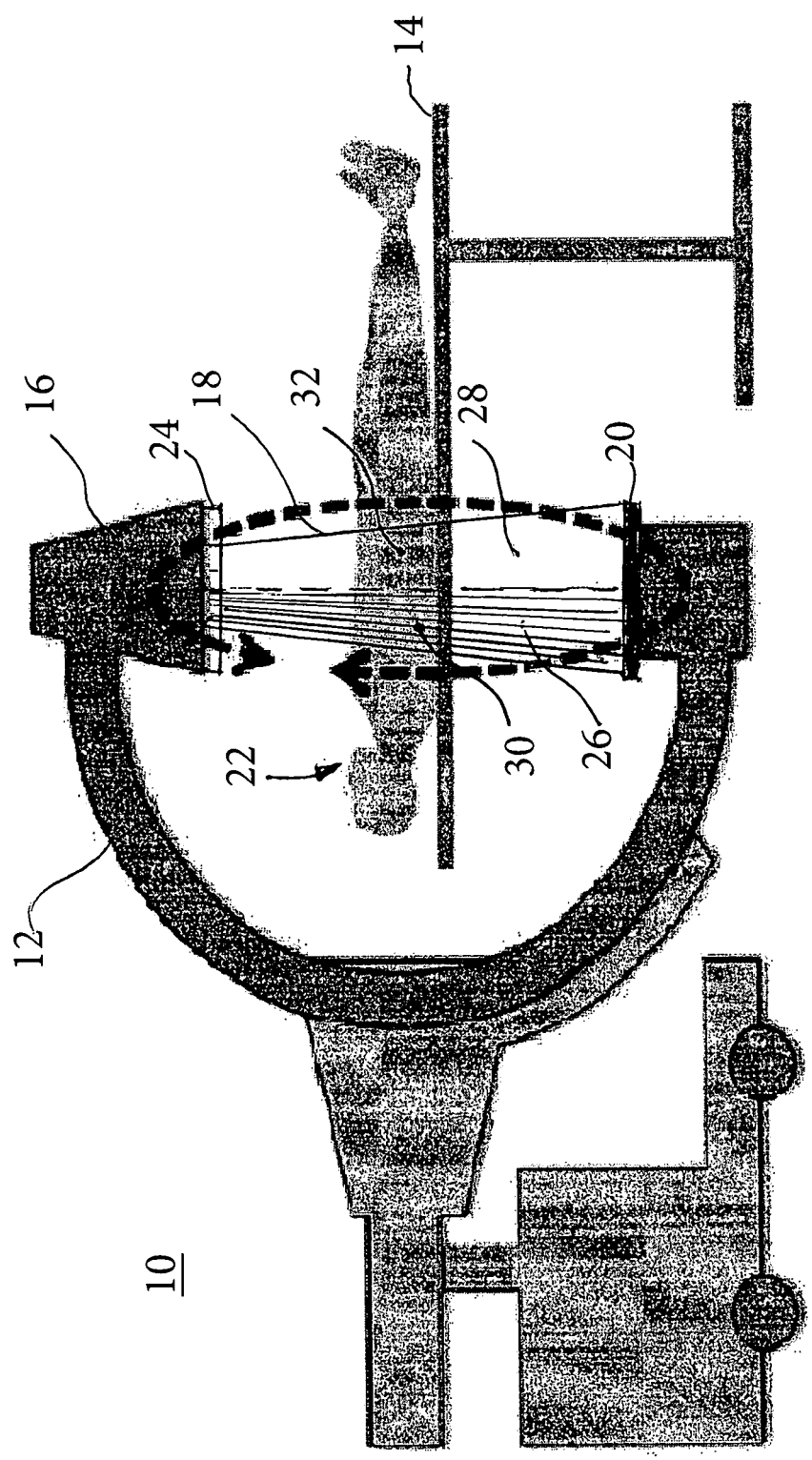
FIG. 7 shows an example of an embodiment of a medical imaging system for use in performing the medical imaging methods and variations thereof described herein.

The medical imaging method is performed on a medical imaging system, for example, the medical imaging system 10 illustrated in FIG. 7. In on embodiment, the medical imaging system 10 comprises a rotating gantry or C-arm 12 configured to rotate, for example, about an examination table 14. Supported by the C-arm 12 are a radiation source 16 to emit a radiation beam 18 and a radiation detector 20. The examination table 14 is configured to support a volume of interest 22, such as a patient. The system 10 also comprises a collimator 24 to vary collimation of the emitted beam radiation beam 18 so as, for example, to change at least part-time a field of view (26, 28) of said emitted radiation beam 18 so that there are at least a first part 30 and a second part 32 of said volume of interest 22 such that, when said first part 30 of said volume of interest is imaged, said second part 32 of said volume of interest is shuttered, as illustrated in FIG. 7, and when said second part of said volume of interest is imaged, said first part of said volume of interest is shuttered (not shown).

In the step S1 of emission, a radiation beam is emitted by a radiation source which is supported by a C-arm of a medical imaging system. Not all the emitted radiation beam will image the volume of interest, which can be a part of a patient, because part of this emitted radiation beam will be shuttered by a dynamic or variable collimation. The C-arm is rotating.

In the step S2 of collimation variation between rotations, the C-arm stops rotating at a moment, and during this moment, the collimation of the emitted radiation beam is changed from a former collimation position to a new collimation position. The C-arm then rotates again.

In the step S3 of quick rotation, during quick rotation of the C-arm, for example during one rotation turn, the collimation of the emitted radiation beam stays unchanged, and therefore the whole rotation turn is performed with the new but constant collimation position. Each collimation position is used successively on a different rotation turn.

In the step S4 of detection, the emitted radiation beam with the new constant collimation position reaches the radiation detector of the C-arm where it is detected and then processed. Thanks to the collimation of the emitted radiation beam, there is a limited scattered radiation among the detected radiation on the sensitive surface of the radiation detector.

Dynamic collimation takes advantage of multiple rotations to capture several tomographic acquisitions, which may be for example rotational or helical, with distinct fields of view composing a tiling of the sensitive surface of the radiation detector. Therefore, with this tiling, at each moment, a part of the sensitive surface of the radiation detector is illuminated by an image of a portion of the volume of interest while another part of the sensitive surface of the radiation detector is shuttered and then can only receive scattered radiation.

The simple implementation of FIG. 1 captures one tile per rotation turn. Each acquisition thus contains, on the one side an illuminated area of the sensitive surface of the radiation detector with reduced scattered radiation, and on the other side a complementary area of the sensitive surface of the radiation detector where scattered radiation is estimated for further subtraction, leading that way to a further reduction of scattered radiation. For each application, a specific set of the number of rotations and of the sizes and of the shapes of the tiles can be adapted.

FIG. 2 shows an example of another embodiment of a medical imaging method varying the collimation of the emitted radiation beam according to the invention. The medical imaging method varying the collimation of the emitted radiation beam comprises a step S5 of emission, a step S6 of slow rotation, a step S7 of collimation variation during rotation, a step S8 of detection.

In the step S5 of emission, a radiation beam is emitted by a radiation source which is supported by a C-arm of a medical imaging system. Not all the emitted radiation beam will image the volume of interest, which can be a part of a patient, because part of this emitted radiation beam will be shuttered by a dynamic or variable collimation. The C-arm is rotating.

In the step S6 of slow rotation, during slow rotation of the C-arm, for example during one rotation turn, the collimation of the emitted radiation beam will be often or even continuously changed, and therefore the whole rotation turn is performed with several collimation positions with permanent switching between these collimation positions.

In the step S7 of collimation variation during rotation, during each angular portion of the slow, maybe even incremental, rotation of the C-arm corresponding to step S6, switching between both or even between several collimation positions (if more than two of them) is performed. Therefore, during a rotation turn, the complete set of collimation positions has been used several times, maybe many times, for example more than ten times. All collimation positions are used successively and several times on the same rotation turn.

In the step S8 of detection, the emitted radiation beam with the new constant collimation position arrives on the radiation detector of the C-arm where it is detected and then processed. Thanks to the collimation of the emitted radiation beam, there is a limited scattered radiation among the detected radiation on the sensitive surface of the radiation detector.

In the implementation of FIG. 2, where the dynamic collimation is fast with respect to the rotation speed of the C-arm, the change of beam shape is performed during the rotation, allowing a complete tiling to be acquired over a narrow angular sector during a single rotation, this complete tiling being acquired repeatedly over the different narrow angular sectors during a single rotation. This implies that T tiles are acquired in the same time frame as a full projection image, hence requiring a faster imaging chain, which means faster tube exposure and faster detector read out, than what was needed for the implementation of FIG. 1. Indeed, given an image chain performance, it suffices to lower the rotation speed T times to fill the previous requirements. In addition, intermediate compromises can be chosen, which means T tiles acquired in R rotations with T/R tiles per angular sector of the rotation of the C-arm. Therefore, each illuminated tile contains a scatter component that is reduced in magnitude and estimated in the shadow zone to be further subtracted, while the stitching of the tiles give rise to a full projection at each sampled angulation. In an option, the tiling may also be overlapping.

Different tiling types providing advantages for producing higher image quality in tomography will now be described. A first type of tiling will be described in relation to FIGS. 3A to 3D. A second type of tiling will be described in relation to FIGS. 4A to 4E. A third type of tiling will be described in relation to FIGS. 5A to 5C. A fourth type of tiling will be described in relation to FIGS. 6A to 6D.

FIG. 3A to 3D show an example of a first type of tiling and of the associated scanning of the sensitive surface of the radiation detector used to perform a medical imaging method varying the collimation of the emitted radiation beam according to the invention. The associated scanning is preferably an associated linear scanning. On each of the FIGS. 3A to 3D, there is a different collimation position of the blades, and there is a different position of the illuminated strip 1 on the sensitive surface 3 of the radiation detector. The sensitive surface 3 of the radiation detector can be a square having a side L. Preferably, the sensitive surface 3 of the radiation detector is a rectangle. The illuminated strip 1 corresponds to an image of a part of the volume of interest. The illuminated strip 1 has a length L which is equal to the side L of the sensitive surface 3 of the radiation detector. The illuminated strip 1 has a width x which is smaller than the side L of the sensitive surface 3 of the radiation detector.

The portions 2 are shuttered portions of the emitted radiation beam. So, the signal received on the corresponding part of the sensitive surface 3 of the radiation detector corresponds to scattered radiation that does not contribute to image formation. This scattered radiation is preferably either discarded or used as an estimate of the scatter radiation within the illuminated strip that is preferably subtracted from the measured radiation in the illuminated strip during subsequent processing. All along the FIGS. 3A to 3D, it can be seen that the illuminated strip 1 is scanning the sensitive surface 3 of the radiation detector from top to bottom, the illuminated strip 1 being translated from top to bottom of the sensitive surface 3 of the radiation detector. At least L/x different discrete positions of the blades are needed for a full scan of the sensitive surface 3 of the radiation detector. Discrete scanning allows for a non-overlapping tiling. Scanning can also be continuous.

The dynamic collimation defines a narrow strip in the direction of the axis of rotation of the C-arm, and a long strip orthogonally to this axis of rotation of the C-arm. The illuminated strip 1 is moved from the top to the bottom of the sensitive surface 3 of the radiation detector, or alternatively the bottom to the top of the sensitive surface 3 of the radiation detector. Depending on the specific application, there can be a parameterization by the number of turns, the speed of rotation of the C-arm, the width of the illuminated strip 1 and the translation speed of the illuminated strip 1.

Different examples of tiling with a square flat-panel sensitive surface 3 of the radiation detector using an illuminated strip 1 of relative length 100% of the side of the sensitive surface 3 of the radiation detector in the direction orthogonal to the axis of rotation of the C-arm, and of relative width 100x/L % of the side of the sensitive surface 3 of the radiation detector in the direction of the axis of rotation of the C-arm, can be used. The shadow zone, corresponding to shuttered part of the sensitive surface 3 of the radiation detector, has a relative width y=100(1−x/L) %. A given tile thus covers 100x/L % of the projection to targeted field of view. For example, 100x/L %>50%, a maximum of two turns is needed to fully cover the targeted field of view, and the tiling is overlapping. For example, if 100x/L %=50%, the tiling is optimized for two turns without overlapping. For example, if 100x/L %<50%, the tiling will require more than two turns.

FIG. 4A to 4E show an example of a second type of tiling and of the associated scanning of the sensitive surface of the radiation detector used to perform a medical imaging method varying the collimation of the emitted radiation beam according to the invention. On each of the FIGS. 4A to 4E, there is a different collimation position of the blades, and there is a different position of the illuminated strip 1 on the sensitive surface 3 of the radiation detector. The sensitive surface 3 of the radiation detector can be of rectangular shape with a length L and a width w. The illuminated strip 1 corresponds to an image of a part of the volume of interest. The illuminated strip 1 has a width w which is equal to the width w of the sensitive surface 3 of the radiation detector. The illuminated strip 1 has a length l which is smaller than the length L of the sensitive surface 3 of the radiation detector.

The portions 2 are shuttered portions of the emitted radiation beam. So, the signal received on the corresponding part of the sensitive surface 3 of the radiation detector corresponds to scattered radiation that does not contribute to image formation. This scattered radiation is preferably either discarded or used as an estimate of the scatter radiation within the illuminated strip that is preferably subtracted from the measured radiation in the illuminated strip during subsequent processing. All along the FIGS. 4A to 4E, it can be seen that the illuminated strip 1 is scanning the sensitive surface 3 of the radiation detector from left to right, the illuminated strip 1 being translated from left to right of the sensitive surface 3 of the radiation detector. At least L/l different discrete positions of the blades are needed for a full scan of the sensitive surface 3 of the radiation detector. Discrete scanning allows for a non-overlapping tiling. Scanning can also be continuous.

Computed tomography scanner gantry can rotate their narrow and long illuminated strip 1 extremely fast, thus allowing for multiple rotations of the gantry. Each rotation can sample only a sub-fan of the strip. Fast rotation can be substituted with fast dynamic collimation so that each sub-fan is collected successively over a narrow angular sector. Again, each tile has a scatter component that is reduced in magnitude and estimated in the shadow zone for further removal.

Figures 3A, 3B, 3C, 3D:
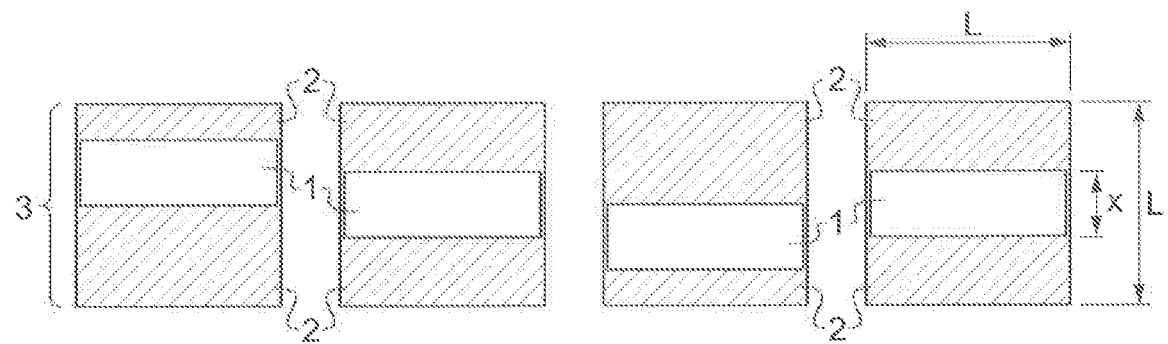
FIG. 3A to 3D show an example of a first type of tiling and of the associated scanning of the sensitive surface of the radiation detector used to perform a medical imaging method varying the collimation of the emitted radiation beam according to the invention.
Figures 4A, 4B, 4C, 4D, 4E:
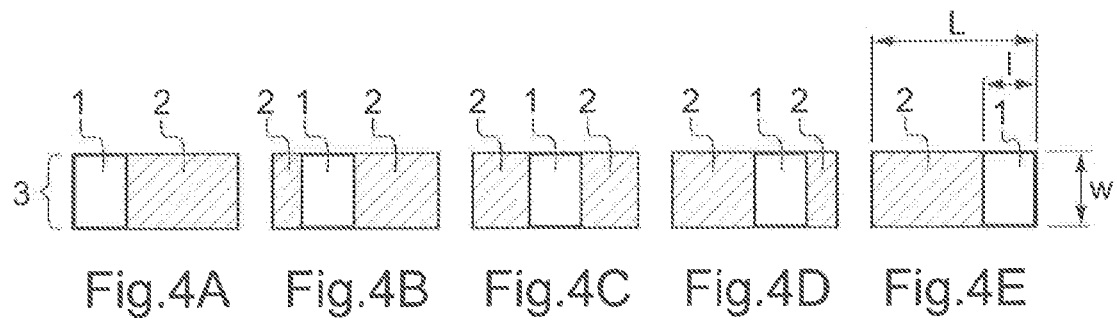
FIG. 4A to 4E show an example of a second type of tiling and of the associated scanning of the sensitive surface of the radiation detector used to perform a medical imaging method varying the collimation of the emitted radiation beam according to the invention.
Figures 5A, 5B, 5C:
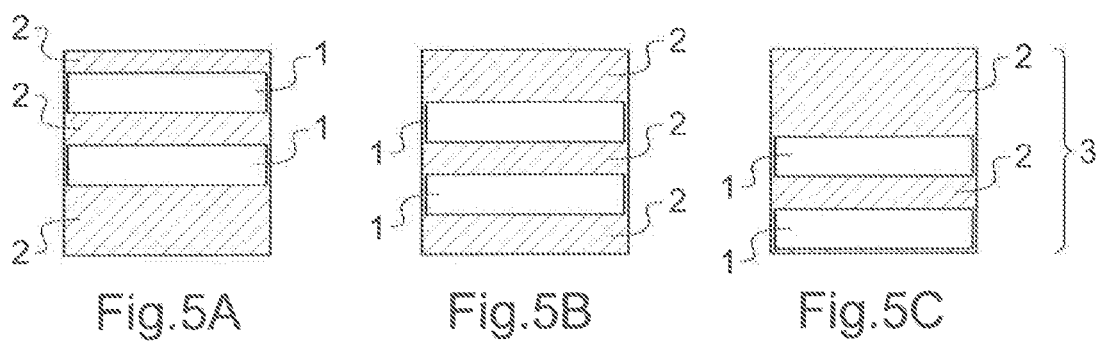
FIG. 5A to 5C show an example of a third type of tiling and of the associated scanning of the sensitive surface of the radiation detector used to perform a medical imaging method varying the collimation of the emitted radiation beam according to the invention.
Figures 6A, 6B, 6C, 6D:
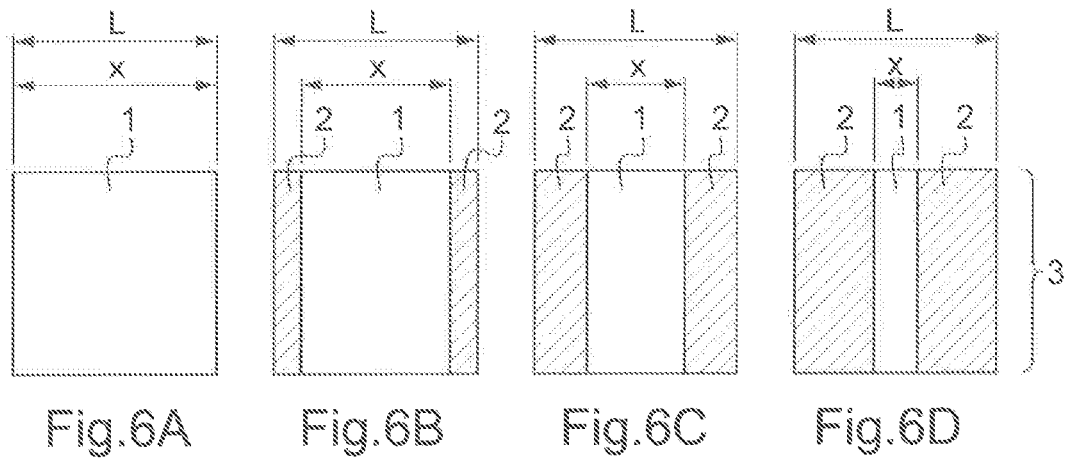
FIG. 6A to 6D show an example of a fourth type of tiling and of the associated scanning of the sensitive surface of the radiation detector used to perform a medical imaging method varying the collimation of the emitted radiation beam according to the invention.

FIG. 5A to 5C show an example of a third type of tiling and of the associated scanning of the sensitive surface of the radiation detector used to perform a medical imaging method varying the collimation of the emitted radiation beam according to the invention. Those figures are quite similar to FIGS. 3A to 3D except that there are two illuminated strips instead of one. On each of the FIGS. 5A to 5C, there is a different collimation position of the blades, and there are different positions of several illuminated strips 1 on the sensitive surface 3 of the radiation detector. Here there are two different illuminated strips 1, but there could be more of them. The sensitive surface 3 of the radiation detector is preferably a square. The illuminated strips 1 correspond to images of parts of the volume of interest. The illuminated strips 1 each have a length which is equal to the side of the square of the sensitive surface 3 of the radiation detector. The illuminated strips 1 each have a width which is smaller than the side of the sensitive surface 3 of the radiation detector. The sum of the respective widths of the illuminated strips 1 also is smaller than the side of the sensitive surface 3 of the radiation detector.

The portions 2 are shuttered portions of the emitted radiation beam. So, the signal received on the corresponding part of the sensitive surface 3 of the radiation detector corresponds to scattered radiation that does not contribute to image formation. This scattered radiation is preferably either discarded or used as an estimate of the scatter radiation within the illuminated strip that is preferably subtracted from the measured radiation in the illuminated strip during subsequent processing. All along the FIGS. 5A to 5C, it can be seen that the illuminated strips 1 are scanning the sensitive surface 3 of the radiation detector from top to bottom, the illuminated strips 1 being translated from top to bottom of the sensitive surface 3 of the radiation detector. Here again, scanning can be discrete or continuous.

The scatter estimation obtained from the measurements in the shuttered part of the sensitive surface 3 of the radiation detector is most valid in the vicinity of this shuttered part. The best estimation of the scattered radiation contribution within an illuminated area is obtained at the edges of this area, as happens with the previously presented strip sliding tiling explained in more detail in relation to FIGS. 3A to 3D. Alternatively, with this implementation presented with respect to FIGS. 5A to 5C, a higher speed of measurement can be obtained with a collimator made of several leaves, so that several illuminated strips 1 are illuminated at once with scattered radiation measurement readings at their edges.

FIG. 6A to 6D show an example of a fourth type of tiling and of the associated scanning of the sensitive surface of the radiation detector used to perform a medical imaging method varying the collimation of the emitted radiation beam according to the invention. On each of the FIGS. 6A to 6D, there is a different collimation position of the blades, and there is a different extent of the illuminated strip 1 on the sensitive surface 3 of the radiation detector. The illuminated strip 1 stays always centered in the middle of the sensitive surface 3 of the radiation detector, at the same distance from both the left and right extremities of the sensitive surface 3 of the radiation detector. The sensitive surface 3 of the radiation detector is preferably a square having a side L. The illuminated strip 1 corresponds to an image of a part of the volume of interest. The illuminated strip 1 has a length L which is equal to the side L of the sensitive surface 3 of the radiation detector. The illuminated strip 1 has a variable width x which is smaller than or equal to the side L of the sensitive surface 3 of the radiation detector.

The portions 2 are shuttered portions of the emitted radiation beam. So, the signal received on the corresponding part of the sensitive surface 3 of the radiation detector corresponds to scattered radiation that does not contribute to image formation. This scattered radiation is preferably either discarded or used as an estimate of the scatter radiation within the illuminated strip that is preferably subtracted from the measured radiation in the illuminated strip during subsequent processing. All along the FIGS. 6A to 6D, it can be seen that the illuminated strip 1 is scanning the sensitive surface 3 of the radiation detector from center to both left and right extremities through widening and narrowing of the illuminated strip 1. Here again, scanning can be discrete or continuous.

A bow-tie filter modulates the emitted radiation beam according to the expected thickness of volume of interest to penetrate. In fan-beam geometry, the magnitude should be decreased as it goes from the center of the sensitive surface 3 of the radiation detector to its edges. By combining overlapping column tiling with radiation intensity modulation, the emitted radiation beam can be adapted depending on the thickness seen by the given tile. This will both reduce the radiation dose to the patient and the scattered radiation magnitude in a very flexible way. Another advantage over the bow-tie filter is that the intensity modulation can be used at constant filtration, so that each tile is seen with the same emitted radiation beam. Filtration introduces a non-uniform hardening of the emitted radiation beam over the field of view that is tedious to correct for. Bow-tie filters are also specifically designed per anatomy. Here, it can be adapted dynamically per projection angle.

In cone-beam geometry, there will be an optimal exposure for each tile. A simple implementation approximates the intensity modulation of a bow tie filter using symmetrical collimators to create overlapping centered strips of increasing width. With T tiles, the central part is exposed T times, while the edges are exposed only once. An optimal exposure scheme can be designed by varying the number of tiles and their width according to the expected shape of the volume of interest to be imaged. For head imaging, a symmetrical collimator will be efficient. For abdominal imaging, flat-panel radiation detectors are comparatively small, so one edge of the radiation detector is likely facing small thickness while the other edge is facing large thickness. A non-symmetrical collimator will be used in that case. The number, width and radiation exposure of the apertures of the collimator can be adapted or changed per image of the rotation of the C-arm, contrary to bow-tie filtering which has a fixed modulation. Here again, the scattered radiation corresponding to the shuttered portion of the sensitive surface 3 of the radiation detector can be subtracted and advantageously used in subsequent processing.

The invention has been described with reference to preferred embodiments. However, many variations are possible within the scope of the invention.

What is claimed is:
1. A medical imaging method comprising:
   emitting a radiation beam from a radiation source of a rotating gantry or C-arm on a volume of interest; and
   varying collimation of said emitted radiation beam so as to change a field of view of said emitted radiation beam so that there are at least a first part and a second part of said volume of interest such that, when said first part of said volume of interest is imaged, said second part of said volume of interest is shuttered, and when said second part of said volume of interest is imaged, said first part of said volume of interest is shuttered, wherein said collimation is varied during a rotation turn of said gantry or C-arm as said gantry or C-arm rotates, wherein the rotation turn is a full 360 degree rotation of said gantry or C-arm, and both the first and second parts of said volume of interest are imaged during the rotation turn.

2. The medical imaging method according to claim 1, wherein said gantry or C-arm is rotated about an examination table which stays immobile during gantry or C-arm rotation.

3. The medical imaging method, according to claim 1, wherein said gantry or C-arm is rotating so as to perform three dimensional imaging.

4. The medical imaging method according to claim 1, wherein said varying collimation is periodical, said gantry or C-arm rotation is periodical, and wherein a varying collimation frequency is equal to or higher than a rotation frequency of said gantry or C-arm.

5. The medical imaging method according to claim 1, wherein said varying collimation changes said field of view size whereas said varying collimation does not change said field of view central position.

6. The medical imaging method according to claim 5, wherein said varying collimation changes said field of view size such as to perform an intensity modulation on said emitted radiation beam.

7. The medical imaging method according to claim 1, wherein said varying collimation changes said field of view central position whereas said varying collimation does not change said field of view size.

8. The medical imaging method according to claim 1, wherein said varying collimation moves a position of said emitted radiation beam so that the radiation beam scans at least part of a sensitive surface of a radiation detector of said gantry or C-arm.

9. The medical imaging method according to claim 8, wherein said scanning is a linear scanning.

10. The medical imaging method according to claim 1 wherein said varying collimation moves respective positions of at least two emitted radiation beams so that said beams respectively scan complementary portions of at least part of a sensitive surface of a radiation detector of said gantry or C-arm.

11. The medical imaging method according to claim 1, wherein said rotating gantry or C-arm rotates alternatingly clockwise and counter-clockwise.

12. The medical imaging method according to claim 1, wherein said varying collimation shutters at least one third of said emitted radiation beam.

13. The medical imaging method according to claim 1, wherein, when a radiation detector of said gantry or C-arm receives said emitted radiation beam on a first part of a sensitive surface of the radiation detector and a second part of the sensitive surface of the radiation detector is shuttered by said varying collimation, then a level of radiation detected on said second part of the sensitive surface of the radiation detector is calculated to be a level of scattered radiation, and wherein said calculated scattered radiation is then subtracted from a level of radiation detected on said first part.

14. A medical imaging system comprising:
   a rotatable gantry or C-arm comprising a radiation source and a collimating device,
   said radiation source configured to emit a radiation beam on a volume of interest when said gantry or C-arm rotates, and
   said collimating device configured to vary collimation of said emitted radiation beam so as to change a field of view of said emitted radiation beam so that there are at least a first part and a second part of said volume of interest such that, when said first part of said volume of interest is imaged, said second part of said volume of interest is shuttered, and when said second part of said volume of interest is imaged, said first part of said volume of interest is shuttered, and wherein said collimating device varies collimation during a rotation turn of said gantry or C-arm as said gantry or C-arm rotates, wherein the rotation turn is a full 360 degree rotation of said gantry or C-arm, and both the first and second parts of said volume of interest are imaged during the rotation turn.

* * * * *